United States Patent
Hirschman (12)

(10) Patent No.: US 6,355,226 B1
(45) Date of Patent: Mar. 12, 2002

(54) TOPICAL TREATMENT OF SKIN DISEASE AND EYE AFFLICTIONS

(75) Inventor: Shalom Z. Hirschman, Riverdale, NY (US)

(73) Assignee: Advanced Viral Research Corp., Hallandale, FL (US)

( * ) Notice: Subject to any disclaimer, the term of this patent is extended or adjusted under 35 U.S.C. 154(b) by 0 days.

(21) Appl. No.: 09/650,554

(22) Filed: Aug. 30, 2000

Related U.S. Application Data

(63) Continuation-in-part of application No. 08/923,343, filed on Sep. 4, 1997, now abandoned, which is a continuation-in-part of application No. 08/834,189, filed on Apr. 15, 1997, now abandoned.

(51) Int. Cl.$^7$ .............................. A61K 9/12; A61F 13/00
(52) U.S. Cl. ........................... 424/45; 424/434; 514/969
(58) Field of Search .................... 424/45, 434; 514/969

Primary Examiner—Thurman K. Page
Assistant Examiner—Rachel M. Bennett
(74) Attorney, Agent, or Firm—Cohen, Pontani, Lieberman & Pavane

(57) ABSTRACT

A method of treating patients having viral infections including herpes simplex virus 1 and 2 infections and human papillomavirus infections by topically administering Product R, a peptide-nucleic acid preparation, by itself or in a composition comprising Product R and other pharmaceutically acceptable carriers for topical administration, is disclosed.

24 Claims, No Drawings

TOPICAL TREATMENT OF SKIN DISEASE AND EYE AFFLICTIONS

RELATED APPLICATIONS

This application is a continuation-in-part of U.S. application Ser. No. 08/923,343, filed on Sep. 4, 1997 now abandoned which is a continuation-in-part of U.S. application Ser. No. 08/834,189 filed by Shalom Z. Hirschman on Apr. 15, 1997, entitled "TOPICAL TREATMENT OF SKIN DISEASES AND EYE AFFLICTIONS" now abandoned. The contents of application Ser. Nos. 08/923,343 and 08/834,189 are hereby incorporated by reference in their entirety.

BACKGROUND OF THE INVENTION

1. Field of the Invention

The present invention relates to a preparation for topical treatment of skin or eye diseases caused by viral infections.

2. Description of the Related Art

Treatment of viral diseases in humans is a major focus of medical science. While some progress has been made, viral infections are still among the diseases most difficult to treat. Despite growing understanding of viral diseases along with improved techniques for detecting and treating them, few antiviral drugs have proved effective. Some viral diseases such as HIV are life threatening; others such as herpes simplex virus and influenza virus continue to cause severe problems. Further, new viral diseases constantly appear as an inevitable consequence of evolution. Thus, searching for a novel and effective way of treating viral diseases remains imperative and challenging.

Product R[1] emerged as an antiviral product in the 1930's. While it was originally believed to be a product composed of peptone, peptides and nucleic acids (fully defined hereafter), the precise composition remains unidentified. Nevertheless, Product R has demonstrated an ability to inhibit rapidly the course of several viral diseases. It is nontoxic, miscible with tissue fluids and blood sera and free from anaphylactogenic properties.

[1]. The agent is known under the trademark "Reticuloses", a trademark of Advanced Viral Research Corp.

Despite these early promising clinical reports, systematic studies have rarely been performed to establish clinical utility. Optimum dosages of Product R for treating viral infections as indicated above have been poorly investigated. In fact, most of the clinical reports lacked necessary controls and statistically sufficient samples for evaluating the effectiveness of Product R. Note, two earlier publications challenged that Product R failed to demonstrated antiviral activity. In light of this background, the present status of the art of using Product R in treating viral infections remains questionable. Close examination of the development history of Product R reveals no meaningful pattern that could be followed to designate a treatment for a particular viral infection, for viruses causing those infections are extremely diversified in their genetic traits or/and pathogenesis. In addition, earlier clinical applications described Product R only as an agent to be administered alone. Product R has never been suggested to be applied in combination with other antiviral drugs; nor has Product R been administered for a period longer than about two months. Given the limits of prior art, developing new treatment strategies using Product R is desirable.

In developing an antiviral agent, it is well known that inhibitory activity of an antiviral agent against a particular virus cannot be equated with its inhibitory effect against another virus. For example, acyclovir has proved to be specifically effective against herpes simplex 1 and 2 (HSV 1 and 2) but not against cytomegalovirus (CM), even though both HSV and CM belong to the same herpesvirus family, sharing certain genetic features. The specificity of acyclovir rests on the activity of the thymidine kinase gene unique to HSV 1 and 2, indicating that a distinctive feature of each individual virus forms a basis for developing an antiviral agent specifically against this very virus. In other words, treatment of a viral infection using a certain antiviral agent does not necessarily indicate that the same agent will produce the same effect when used for treating other viral infections. The genetic diversity of viruses further mandates that an attempt to be made to discern the effectiveness of a new application of an antiviral agent to a different virus.

An antiviral agent usually interacts with molecules involved in different stages of viral infections: in early events such as adsorption, penetration (internalization), and uncoating; in virus replication characteristic for each virus genome and components of the nucleoprotein complex; and in the chemistry of metabolic pathways. The best targets for inhibition by an antiviral agent are molecules serving a function unique to the virus, with no analogous counterpart in host cells. In order to identify the virus-specific molecule with which a putative antiviral agent interacts, it is important to characterize viruses in terms of particle and genome structure, as well as to define specific biochemical events that occur in infected cells. Although progress has been made in discovering molecules necessary for virus adsorption, replication and metabolism, current knowledge remains insufficient to explain many aspects of these events. Consequently, not every antiviral agent's function is fully defined in terms of its interaction with a target virus through one or a series of the indicated events; much less is understood where an antiviral agent is employed to treat a new viral infection, especially if the antiviral agent has been poorly characterized. Without the knowledge of a virus' genetic traits and the chemical properties of an antiviral agent, treatment of a viral infection becomes unpredictable.

HSV, is known to cause fever blisters and cold sores, among the most prevalent viral infection. There are two HSV strains. Type-1 strain commonly causes herpes labialis located on a lip, and keratitis, an inflammation of the cornea. Type-2 is usually located on or around genital area and is generally transmitted primarily by direct contact with herpetic sores or lesions. Generally, HSV 1 occurs above the waist and HSV 2 occurs below the waist.

Estimated frequency and location of oral (HSV 1) and genital (HSV 2) infections are about half million of primary cases of type-1 per year, with 98 million of recurrent cases per year in the United States alone. Of the genital type-2 cases, there are around 500,000 cases of primary genital herpes with 3–9 million of recurrent cases per year in the United States.

HSV infection is a recurrent infection characterized by the appearance on the skin or mucous membranes of single or multiple clusters of small vesicles, filled with clear fluid on slightly raised inflammatory bases. These symptoms usually accompany a flu or some such other state where the body resistance is low. HSV is very infectious and it is rapidly and easily transferable by contact.

Herpetic lesions may appear anywhere on the skin or mucosa, but are more frequent about the mouth, on the lips, on the conjunctiva and cornea, and on or around the genitalia. Following a short prodromal period of tingling discomfort or itching, small tense vesicles appear on the erythematous base. Single clusters vary in size from 0.1 to 1.5 cm. The vesicles persist for a few days, then begin to dry, forming a thin yellowish crust. Healing is long and usually begins 7–10 days after onset of the viral infection and is complete by about 21 days. Healing may be slower, with secondary inflammation, in moist body areas. Individual herpetic lesions usually heal completely but recurrent lesions at the same site may cause atrophy and scarring. It will be appreciated that the herpes simplex outside or inside mouth, lips, cheeks, chin and particularly on or around the genitalia is very painful and uncomfortable as it burns or itches, as well as ungainly, with an often open sore on the lip and, particularly as it does on recurrence, leaving the ugly lesions on or around lips.

The HSV 2 has even greater and more severe, if possible, consequences. Due to its location on or around the genital area, a social stigma attaches to this type of herpes infection which is categorized as a venereal disease. The viral disease itself is much the same as the HSV 1. Initial and recurring attacks, similar but probably more severe than those of type-1, occur in the neighborhood of the genital organs. The initial attack begins with swelling, reddening, and pain in the area surrounding the site of infection with the inflammation developing and extending over the whole groin, thighs and buttocks. This is accompanied by a low-grade fever, mild flu-like symptoms and swelling of the lymph glands in the groin. The development of small, blister like sores soon follows over much of inflamed area rapidly becoming grayish yellow and ulcerous. These blisters typically last for about two weeks. The symptoms in recurrent episodes are generally not so severe but nonetheless unpleasant and uncomfortable. The recurrence may occur as often as several times a month.

Treatment of genital herpes is primarily by systemic administration of antiviral drugs as described above, for example by IDU and trifluridine (TFT) with all dangers connected with their high cytotoxicity, with ARA-A, another antiviral with somewhat less toxicity, and acyclovir or bromovinyldeoxyuridine which are both enzyme inhibitors semi-specific to virus replication. All these agents are given primarily systemically and have high probability to cause severe side effects, as discussed above. Moreover, none of these agents is a selective inhibitor of only the herpes simplex virus replication but they effect also a replication of normal cells. Therefore, when used in doses large enough to seek and destroy all the active herpes viruses dormant in the sensory ganglia, these compounds may also be highly disruptive to the normal DNA in the host cells in which the virus multiplies. This is a highly undesirable result since the replication of normal cells is also effected. The topically administered acyclovir ointment seems to be effective in the treatment of primary first occurrence of genital herpes infection but has little if any, effect on recurrent genital herpes disease.

Thus, it would be advantageous to have available treatment of genital herpes which would prevent development of painful sores and inflammation in the genital area, prevent their recurrence and yet be innocuous enough toxicologically so that no systemic administration of cytoxic chemical substances is necessary or needed.

Another form of viral herpes disease is so called herpes zoster, commonly known as shingles. Herpes zoster is a disease of middle or old age characterized by extreme pain in a limited area of the upper body or face and an outbreak of small pimply blisters in the same area usually along the nerve branches. The herpes zoster is caused by varicella-zoster virus, the same virus that causes chickenpox. Herpes zoster is an acute central nervous system infection involving primarily the dorsal root ganglia and characterized by vesicular eruption and neuralgic pain in the cutaneous areas supplied by peripheral sensory nerves arising in the affected root ganglia in which the inflammatory changes occur.

There is no specific therapy for this extremely painful viral infection. Corticosteroids, if given early, may relieve pain in severe cases. Aspirin and other anti-inflammatories or antiviral agents systemically may alleviate the pain. However, these agents have undesirable side effects.

Thus, it would be extremely important to find an agent which would alleviate the pain connected with the symptomatically occurring blisters during herpes zoster attack.

Another viral infection which may severely effect the patient in that it disfigures patient's face is varicella also know as chickenpox caused by varicella virus. This is a rare form of chickenpox in which the eruption leads to a gangrenous ulceration. There is severe scarring (pock marking) following the healing of the ulceration which never disappears and the person's face is forever disfigured. Moreover, there is no treatment known or prevention for the chickenpox or the subsequent scarring.

Consequently, it would be desirable to have available treatment and/or prevention for the gangrenous ulceration before it results in the scars.

Another highly unpleasant and painful conditions are genital warts caused by human papillomavirus (HPV). Not only this condition is unpleasant and painful but it may also contribute to cervical and genital cancers.

Thus, it would be advantageous and highly desirable to provide an effective treatment against genital warts.

SUMMARY OF THE INVENTION

An object of this invention is to provide a preparation that is effective in topical treatment of infections caused by viruses including HSV 1 and 2, herpes zoster, genital warts chickenpox and adenovirus, etc. This has been accomplished by using Product R alone or in a pharmaceutical composition containing Product R.

One aspect of the present invention relates to a method for treating patients having skin diseases caused by viral infections by administering Product R topically to the area of the infections, using Product R alone or in a pharmaceutical composition containing Product R.

Another aspect of the present invention relates to a method for treating patients having eye afflictions caused by viral infections by administering Product R to the patients' eyes, using Product R alone or Product R with pharmaceutical acceptable carriers.

Still another aspect of this invention relates to a pharmaceutical composition for topical treatment containing an effective treatment amount, i.e. at least 50% by weight, of Product R.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

DETAILED DESCRIPTION OF THE PRESENTLY PREFERRED EMBODIMENTS

"Viral infection" refers to all types of infections caused by viruses including but not limited to herpes simplex, genital herpes, herpes zoster, chickenpox or genital warts (HPV).

"Pharmaceutically acceptable carriers" means any and all additives which are acceptable in the pharmaceutical sciences, and may be a high molecular weight polymeric agents such as cellulosic polymers hydroxyethylcellulose, hydroxypropylcellulose, methylcellulose, vinylic polymers, polyvinylpyrolidone, polyvinyl alcohol, polyethylene glycol, petrolatum, talcum or other additives or binders.

As used herein, Product R is the product manufactured by Advance Viral Research Corp according to either of the following methods.

Method I for Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Carefully add while stirring about 16.5 g of sodium hydroxide (reagent grade ACS) and continue stirring until sodium hydroxide completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/ml, the final volume is approximately 5 liters. The pH is then adjusted with either concentrated HCl (reagent grade ACS) or 1.0 normal Noah to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

Method II for Preparing Product R

Suspend about 35.0 g of casein, about 17.1 g of beef peptone, about 22.0 g of nucleic acid (RNA), about 3.25 g bovine serum albumin in about 2.5 liters of water for injection USP at about 3 to 7° C. in a suitable container and gently stir until all the ingredients have been properly wet. Slowly add while stirring about 11.75 ml of hydrochloric acid (reagent grade ACS) and continue stirring until hydrochloric acid is completely dissolved. Autoclave at about 9 lbs pressure and 200–230° F. for a period of time until RNA is completely digested, for example, about 4 hours. At the end of the period, the autoclave is stopped and the reaction flask and contents are permitted to slowly cool to ambient temperature. Then cool for at least six hours at about 3–8° C. The resulting solution is filtered through 2 micron and 0.45 micron filters using inert gas such as nitrogen or argon at low pressure (1–6 psi). In a similar manner the solution is filtered again through 0.2 micron pyrogen retention filters. The resulting filtrate is sampled and assayed for total nitrogen. A calculation is then performed to determine the quantity of cooled water for injection to be added to the filtrate to yield a diluted filtrate with a nitrogen content between about 165–210 mg/mil, the final volume is approximately 5 liters. The pH is then adjusted with either concentrated HCL (reagent grade ACS) or 35% (w/v) of Noah to about 7.3–7.6 range. The diluted solution is then filtered again through 0.2 micron filters with inert gas at low pressure. The final filtrate is then filled and sealed into 2 ml glass ampules while in an inert gas atmosphere. The ampules are collected and autoclave for final sterilization at 240° F. and 20 to 30 pounds pressure for about 30 minutes. Following the sterilization cycle, the ampules with Product R are cooled and washed.

All quantities are subject to plus or minus 2.5% variation for pH, volume, and analytical adjustments.

The composition, biochemical and physical properties of Product R manufactured according to the above described methods were analyzed, the results of which are disclosed in U.S. patent application Ser. No. 09/344,095, the content of which is hereby incorporated by reference in its entirety. Generally, Product R comprises molecules of nucleotides and peptides, which absorbs light at wavelengths 230 nm, 260 nm and 280 nm such that 260/280 nm absorption ratio is about 1.998 and 260 nm/230 nm absorption ratio about 1.359. The molecules of the nucleotides and the peptides has substantial concentrations at molecular weights of 5.2 Kda and 4.3 Kda, While Product R may be formulated in solutions, ointments, creams, gels, sprays or any other form together with pharmaceutically acceptable carriers for topical application, it is preferably applied alone, in either diluted or concentrated form, without further formulation as a topical pharmaceutical agent.

When Product R is used in a pharmaceutical formulation other than by itself, the composition may also contain antimicrobials, including antibiotics, antifungals, and other anti-viral compounds, which may complement or supplement the activity of the basic composition. Suitable antibiotics include tetracycline, polymyxin B or other common antibiotics used in topical compositions, especially over-the-counter formulations. Examples of useful antifungals include tolnaftate and micatin. Examples of anti-virals include interferon, either natural or recombinant, as well as nucleoside analogs, e.g., acyclovir. Counter-irritants such as camphor and menthol, drying agents such as benzyl alcohol, resorcinol and phenol, and astringents such as zinc sulfate and tannic acid can also be added to the composition as can other types of agents such as sunscreens, emollients, preservatives, fragrances, antioxidants, color additives, lubricants, moisturizers or drying agents. For example, a sunscreen, e.g., PABA, can be added to the formula since it is known that cold sores can be triggered by ultraviolet radiation.

The composition can be prepared in almost any relatively inert topical carrier. Generally, the formulation could take several forms, e.g., cream, gel, ointment, wax and solution forms. Each of these formulations may contain Product R as well as microorganism growth inhibitors (preservatives) and other additives above noted. Many such carriers are routinely used and can be obtained by reference to standard pharmaceutical texts. Examples include polyethylene glycols (PEG), polypropylene glycol copolymers (Pluronics), and some water soluble gels.

The preferred carrier is an emulsified cream, but other common carriers such as certain petrolatum or mineral oil-based ointments in which Product R is dispersible can be substituted.

Gels, i.e., thickened aqueous or alcoholic solutions, containing Product R and stabilizers may be clear and/or colored with suitable dyes. Suitable thickeners may include carboxymethylcellulose, polyvinylpyrrolidone or polyacrylic acid salts.

Hydrophilic or hydrophobic ointments may be employed as carriers. However, hydrophobic ointments, such as petroleum jelly, which are based upon hydrocarbon and wax derivatives may not be as efficacious as the hydrophilic ointments because they may impede penetration into the skin. Hydrophilic ointments such as those based upon propylene glycol, polyalkylene glycols, and the Pluronics are therefore preferred for ointment formulations. Propylene glycol, as a base, is preferable to polyethylene glycol.

Wax formulations may be employed in some situations, e.g., for treatment of cold sores, where ease of application is a primary objective.

Solutions, i.e., dilute aqueous preparations containing Product R and preservatives but without substantial concentrations of thickeners, can be sprayed upon the affected surface as by an aerosol pump. This type of delivery may be of value for treating larger areas of painfully sensitive skin in indications such as shingles.

Product R may be applied to eyes without further formulation as eye drops. Alternatively, microorganism growth inhibitors or other pharmaceutically acceptable carriers as indicated above may be added to form a composition suitable for eye application.

In most cases, it is preferred that the pH of the carrier containing the active ingredients is adjusted to a pH of about 6 to 7, using, as buffering agents, ingredients such as borax although other acceptable buffering agents could be used.

Additional additives may include antioxidants, fragrance, color, water, preservatives (either antioxidants or antimicrobials), lubricants, moisturizers, or drying agents.

In any case other than that of Product R used alone, the pharmaceutically acceptable composition should contain Product R at least 50% by weight, preferably, over 90% by weight.

The composition is applied by the patient to the lesions one to six times daily, most preferably beginning immediately after the prodrome is sensed and continuing, until the lesion and accompanying discomfort disappear. Product R should be applied to the entire surface infected by viruses in an amount determined by the size of lesion or prodromal areas, generally, sufficient to cover the lesion or prodromal areas.

The present invention is particularly useful for treating patients having herpes labialis or genital herpes caused by HSV-1 or HSV-2 infections, common warts including genital warts, digital warts and plantar warts inflicted by, for example papillomavirus.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

I claim:

1. A method for treating patients having viral infections with surface manifestation on the skin, mucosa or eyes, comprising topically administering an effective amount for topical treatment of Product R to the area of the infections, wherein said Product R is a peptide nucleic acid composition that absorbs light at wavelengths 230 nm, 260 nm and 280 nm so as to result in 260 nm/280 mn absorption ratio of about 1.998 and 260 nm/230 nm absorption ratio of about 1.359, comprising molecules of nucleotides resulting form a plant RNA and peptides resulting from a mixture of casein, beef peptone and bovine serum albumin, said molecules having non-uniformly distributed molecular weights.

2. A method as in claim 1, wherein said area of the infections is said patients' skin.

3. A method as in claim 1, wherein said area of the infections is said patients' mucosa.

4. A method as in claim 1, wherein said area of the infections is said patients' eyes.

5. A method as in claim 1, wherein said viral infections with surface manifestation on the skin, mucosa or eyes are common warts.

6. A method as in claim 5, wherein said common warts are inflicted by HPV.

7. A method as in claim 1, wherein said viral infections with surface manifestation on the skin, mucosa or eyes are inflicted by HSV-1.

8. A method as in claim 1, wherein said viral infections with surface manifestation on the skin, mucosa or eyes are inflicted by HSV-2.

9. A method for treating patients having viral infections with surface manifestation on the skin, mucosa or eyes, comprising topically administering an effective amount for topical treatment of a composition comprising Product R and pharmaceutically acceptable carriers for topical administration, to the area of the infections, wherein said Product R is a peptide nucleic acid composition that absorbs light at wavelengths 230 nm, 260 nm and 280 mn so as to result in 260 nm/280 nm absorption ratio of about 1.998 and 260 nm/230 nm absorption ratio of about 1.359, comprising molecules of nucleotides resulting form a plant RNA and peptides resulting from a mixture of casein, beef peptone and bovine serum albumin, said molecules having non-uniformly distributed molecular weights.

10. A method as in claim 9, wherein said area of the infections is said patients' mucosa.

11. A method as in claim 9, wherein said area of the infections is said patients' skin.

12. A method as in claim 9, wherein said area of the infections is said patients' eyes.

13. The method as in claim 9, said composition comprising at least 50% by weight of Product R.

14. The method as in claim 9, said composition comprising at least 90% by weight of Product R.

15. The method as in claim 9, wherein said composition is in a form of solution.

16. The method as in claim 9, wherein said composition is in a form of ointment.

17. The method as in claim 9, wherein said composition is in a form of emulsified cream.

18. The method as in claim 9, wherein said composition is in a form of gels.

19. The method as in claim 9, wherein said composition is in a form of wax.

20. The method as in claim 9, wherein said composition is in a aerosol form.

21. A method as in claim 9, wherein said viral infections with surface manifestation on the skin, mucosa or eyes are common warts.

22. A method as in claim 21, wherein said common warts are inflicted by HPV.

23. A method as in claim 9, wherein said viral infections with surface manifestation on the skin, mucosa or eyes are inflicted by HSV-1.

24. A method as in claim 9, wherein said viral infections with surface manifestation on the skin, mucosa or eyes are inflicted by HSV-2.

* * * * *